(12) United States Patent
Summerville

(10) Patent No.: US 6,673,792 B1
(45) Date of Patent: Jan. 6, 2004

(54) BROAD-SPECTRUM ANTI-EMETIC COMPOSITIONS AND ASSOCIATED METHODS

(75) Inventor: James Peter Summerville, Winter Park, FL (US)

(73) Assignee: Upchuck, LLC, Longwood, FL (US)

( * ) Notice: Subject to any disclaimer, the term of this patent is extended or adjusted under 35 U.S.C. 154(b) by 0 days.

(21) Appl. No.: 10/194,868

(22) Filed: Jul. 11, 2002

(51) Int. Cl.[7] .............................................. A61K 31/55
(52) U.S. Cl. ...................................................... 514/221
(58) Field of Search ......................................... 514/221

(56) References Cited

U.S. PATENT DOCUMENTS

| | | |
|---|---|---|
| 4,952,402 A | 8/1990 | Sparks et al. |
| 4,983,586 A | 1/1991 | Bodor |
| 5,011,992 A | 4/1991 | Monkovic et al. |
| 5,024,998 A | 6/1991 | Bodor |
| 5,310,561 A | 5/1994 | Jao et al. |
| 5,811,547 A | 9/1998 | Nakamichi et al. |
| 6,071,927 A * | 6/2000 | Baker et al. ................. 514/278 |
| 6,353,005 B1 * | 3/2002 | Rubin et al. ................. 514/327 |
| 2002/0055495 A1 * | 5/2002 | Jannetta ....................... 514/171 |

* cited by examiner

*Primary Examiner*—James H Reamer
(74) *Attorney, Agent, or Firm*—Preston Gates & Ellis LLP; John W. Wallen, III

(57) ABSTRACT

Broad-spectrum anti-emetic pharmaceutical compositions are disclosed. The discloses broad-spectrum ant-emetics disclosed herein comprise selected neuroreceptor antagonists specifically formulated to treat and prevent to most common forms of emesis. In one embodiment the ant-emetic compositions include lorazepam, diphenhydramine, promethazine, and metoclopramide. The pharmaceutical compositions include, but are not limited to oral and parenteral forms and may include one or more pharmaceutically acceptable excipient.

12 Claims, No Drawings

BROAD-SPECTRUM ANTI-EMETIC COMPOSITIONS AND ASSOCIATED METHODS

FIELD OF THE INVENTION

The present invention comprises anti-emetic compositions and related methods for using same. More specifically, the present invention relates to compositions having more than one anti-emetic ingredient, which act synergistically and/or additively to relieve symptoms associated with emesis

BACKGROUND OF THE INVENTION

Emesis, also referred to as vomiting, is associated with myriad clinical conditions. For example, emesis is often associated with uncomplicated motion sickness, mild gastrointestinal upset caused by infections, food poisoning and adverse drug reactions including cancer chemotherapy. Additionally, emesis provides an elimination mechanism for ingested toxins and poisons. Moreover, the colors, smells tastes and textures associated with potentially toxic compounds results in a learned aversion to these substances, thus providing animals with a vital survival mechanism.

Emesis symptoms can range from an unpleasant inconvenience to a debilitating condition causing sever dehydration, weight loss, fatigue, torn esophagus, broken bones and reopening of surgical wounds. Moreover, many forms of chemotherapy and most radiation treatments can induce severe nausea and emesis. Patents that are particularly adversely affected with emesis can become severely dehydrated and malnourished requiring parenteral fluid and dietary supplementation. As a result, many patents find that their life quality is so compromised that they voluntarily remove themselves from life saving chemotherapy. In other patients, the emesis is so severe that physicians must temporarily, or permanently discontinue treatments. Often times the treating physician is without other therapeutic options, consequently the patient goes under treated, or in some cases, untreated.

Unfortunately, emesis is a complex, multifactorial process for which there is presently no therapeutic regime suitable for treating or preventing all underlying biological emesis-related processes. Emesis involves many different neuroreceptors and the biochemical pathways that regulate emesis are varied and complex. Emesis-associated neuroreceptors include neurochemical receptors such as dopamine receptors, 5-hydroxytrytamine (5-HT) receptors, aceytalcholine receptors, histamine receptors, opioid receptors, neurokinin ($NK_1$) receptors, and cannabinoid receptors, as well as mechano-receptors.

Mechano-receptors are generally located in the stomach and small intestines and are activated in response to emetic stimuli and cause the expulsion of stomach and/or intestinal contents. The Mechano-receptors are tension sensors activated in response to the contraction and extension of the stomach and intestines and are the primary receptors associated with bowl occlusion-related emesis.

Neurochemical receptors are located in the stomach, the small intestines and the central nervous system (CNS). These respond to various chemical stimuli including toxins such as cholecystokinin (CCK) peptides, copper sulfate and 5-hydroxytrytamine (5-HT) among others. Copper sulfate-induced vomiting is mediated by $5-HT_4$ receptors, CCK acts via CCK-A receptors and emesis associated with cancer therapies such as irradiation and chemotherapy are medicated by $5-HT_3$ receptors.

There are four 5-HT receptors associated with emesis including $5-HT_3$, $5-HT_{1a}$, $5-HT_{1D}$ and $5-HT_4$. Among the 5-HT receptors involved in emesis, the $5HT_3$ has been identified as the most important receptor involved in cancer therapy-related emesis. $5-HT_3$ receptors are located in the CNS and peripherally in the gut mucosa, nerve endings and primary afferent nerve fibers. Antagonism of the $5-HT_3$ receptors can prevent emesis associated with increased local 5-HT concentrations. $5-HT_{1a}$, $5-HT_{1D}$, and $5-HT_4$ receptors are primarily located in the CNS; however, they also occur in the periphery including the myocardium ($5-HT_4$) and arterioles ($5-HT_{1a}$). The primary dopamine receptor involved in emesis is the $dopamine_2$ ($D_2$) receptor. $Dopamine_2$ antagonists include phenothiazies, butyrophenones, and benzamides; both CNS and gastrointestinal (GI) receptors are blocked.

It has been demonstrated that emesis can be controlled when specific receptor antagonists are administered prior and/or after onset of nausea or emesis. Receptor antagonists act as anti-emetics by blocking receptors in the central nerves CNS and/or GI tract and prevent binding of the target ligand. For example, a dopamine receptor antagonists block dopamine binding thus preventing the neuro-sensory activity associated with dopamine and its associated emetic effects.

Present anti-emetic therapies are composed of neuroreceptor antagonists that target one or two of the receptors that regulate emesis. However, as previously stated, emesis is a complex, multi-factorial process that involves a wide array of neuroreceptors. Therefore, there is a need for broad-spectrum anti-emetic compositions suitable for use with all patients, regardless of the underlying biological process associated with their particular emesis. An ideal broad spectrum anti-emetic composition will comprise a variety of receptor antagonists that block emesis associated receptors preventing them from initiating nausea and the vomiting reflex.

SUMMARY OF THE INVENTION

The present invention is a therapeutic composition for the treatment and prevention of emesis. In one embodiment of the present invention the therapeutic compositions include broad-spectrum medicaments containing specific neuroreceptor antagonists. The neuroreceptors targeted by the medicaments of the present invention include, but are not limited to, dopamine receptors, 5-hydroxytrytamine (5-HT) receptors, aceytalcholine receptors, histamine receptors, opioid receptors, neurokinin ($NK_1$) receptors, and cannabinoid receptors.

The neuroreceptor antagonists of the present invention are selected from the group of compounds including, but not limited to, antihistamines, anti-dopaminergics, and anti-anxiety agents. In specific embodiments of the present invention the anti-emetic compositions comprise at least one benzodiapepine, at least one phenothiazine, at least one diphenhydramine, and at least one metoclopramide.

In one embodiment of the present invention the anti-emetic compositions comprise lorazepam, promethazine, diphenhydramine, and metoclopramide.

In another embodiment of the present invention the anti-emetic compositions comprise from approximately 0.1 to 100 mg/unit of lorazepam, from approximately 0.1 to 100 mg/unit promethazine, from approximately 0.1 to 100 mg/unit diphenhydramine, and from approximately 0.1 to 100 mg/unit metoclopramide, wherein a "unit" is defined as a single drug delivery form.

In yet another embodiment the compositions are drug delivery forms selected from the group consisting of compressed tablets, capsules, caplets, gelcaps, free flowing powders, compressed powders, suppositories, transdermal devices, implantable drug release depots, inhalants, liquids suitable for intravenous (parenteral) use, liquids suitable oral use, and multi-phasic slurries.

In another embodiment of the present invention the drug delivery forms are compounded to provide controlled delivery of the anti-emetic compositions over a predetermined time.

DEFINITION OF TERMS

Prior to setting forth the invention, it may be helpful to an understanding thereof to set forth definitions of certain terms that will be used hereinafter.

Approximately: The term approximately as used herein means an estimated amount of a compound or an estimated distance or temporal interval. When used to denote a numerical value the term approximately includes all values within a range that those having ordinary skill in the art would understand that range to include. For example, and not intended as a limitation, the phrase "from about 0.1 to 100 mg" would include a range of values included, at least from 0.009 to 110 mg and all values in between.

Broad-spectrum: As used herein, "broad-spectrum" refers to anti-emetic compositions that provides treatment or prevention of emesis caused by physical or chemical interactions with a wide range of distinct neuroreceptors.

Depot: As used herein, "depot" or "drug depot" refers to a reservoir containing a composition that is implanted into, or in some fashion connected to a patient such that the compound is delivered to the patient. The depot may or may not regulate the administration of the compound.

Drug delivery form: Any physical state useful in administering a compound of the present invention to a patient.

Parenteral: Administrating the compounds of the present invention in any form or manner that does not involve the intestines.

Patient: A mammalian recipient of the compounds of the present invention.

Percent: Percent or "%" refer to parts per 100.

Percent weight: Percent weight, or weight percent, is defined as the weight of the ingredient in question relative to the total weight of the composition. For example, and not intended as a limitation, an ant-emetic composition of the present invention having 1% lorazepam would have 1 gram of lorazepam per 100 grams of the total composition (i.e., 1 gram of lorazepam plus 99 grams of other ingredients). In those cases where the total amount of active (ant-emetic) ingredient(s) do not total 100%, it is presumed that the difference totaling 100% is made up of pharmaceutically acceptable excipients as defined herein.

Prevent: To preclude an anticipated event from occurring. For example, a very high percentage of patents receiving certain forms of chemotherapy and radiation treatment for cancer will experience mild to severe emesis. Administration of the compounds of the present invention prior to onset of emesis precludes emesis from occurring in these patents, thus they "prevent" emesis.

Treating: Treating, in contrast to preventing, involves the alleviation of symptoms subsequent to the symptoms occurring in the patient.

Unit: "Unit" or "unit dose" as used herein refers to a single doe. The unit may be a pill such as a caplet, capsule, gelcap or tablet. A unit may also be a bolus of drug delivered parenterally or orally. Suppositories, transdermal devices, powdered forms, bi-phasic slurries and drug depots are considered units. The units may or may not include timed release forms.

DETAILED DESCRIPTION

The present invention provides anti-emetic pharmaceutical compositions and methods of treating or inhibiting emesis. The pharmaceutical compositions of the present invention comprise neuroreceptor antagonists selected from the group of compounds including, but not limited to, antihistamines, anti-dopaminergics, and anti-anxiety agents. In specific embodiments of the present invention the anti-emetic compositions comprise at least one benzodiapepine, at least one phenothiazine, at least one diphenhydramine, and at least one metoclopramide.

In one embodiment of the present invention the anti-emetic composition comprises from 0.1 to 100 mg/unit of 7-chloro-5(O-chlorophenyl)-1,3-dihydro-3-hydroxy-2H-1, 4-benzodiazepin-2-one (lorazepam); from 0.1 to 100 mg/unit of 10 H-phenothiazine-10-ethanamine,N,N, αtrimethyl-monohydrate (promethazine); from 0.1 to 100 mg/unit 2-(diphenylmethoxy)-N,N-dimethylethylamine hydrochloride (diphenhydramine) and from 0.1 to 100 mg/unit of 4-amino-5-chloro-N-[2-(diethylamino)ethyl]-2-methoxybenzamide (metoclopramide) and various combinations thereof. As used herein, "unit" shall mean a measured amount of a liquid such as, but not limited to a milliliter, an ounce, a dram; a dosage form such as but not limited to a capsule, tablet, suppository or other bolus; weight amount of a packaged powder or any other configuration where a person having ordinary skill in the art of pharmacy would understand the term "unit" to mean.

Such a compositions typically contains from about 0.1 to 99% by weight (such as 1 to 20% or 1 to 10%) of the present invention's anti-emetic compositions in a pharmaceutically acceptable carrier. Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that may be used include acacia, methylcellulose, sodium carboxymethylcellulose, polyvinylpyrrolidone (Povidone™), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antifungal agent and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as water-for-injection, 0.9% saline, or 5% glucose solution. A suitable insoluble form of the compound may be prepared and administered as a suspension in an aqueous base or a pharmaceutically acceptable oil base, such as an ester of a long chain fatty acid (e.g. ethyl oleate).

Transdermal and topical formulations typically contain a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic regimens.

The pharmaceutical compositions of the present invention are be administered to the patient via conventional means such as oral, subcutaneous, intrapulmonary, transmucosal, intraperitoneal, intrauterine, sublingual, intrathecal, intramuscular or transdermal routes using standard methods. In addition, the pharmaceutical formulations can be administered to the patient via injectable depot routes of administration such as by using 1-, 3-, or 6-month depot injectable or biodegradable materials and methods. Regardless of the route of administration, exemplary dosages in accordance with the teachings of the present invention for these composite compounds range from 0.0001 mg/kg to 60 mg/kg, though alternative dosages are contemplated as being within the scope of the present invention. Suitable dosages can be chosen by the treating physician by taking into account such factors as the size, weight, age, and sex of the patient, the physiological state of the patient, the severity of the condition for which the composite compound is being administered, the response to treatment, the type and quantity of other medications being given to the patient that might interact with the composite compound, either potentiating it or inhibiting it, and other pharmacokinetic considerations such as liver and kidney function. Generally, initial doses will be modified to determine the optimum dosage for treatment of the particular subject. The composite compounds can be administered using a number of different routes including orally, topically, transdermally, intraperitoneal injection, or intravenous injection directly into the bloodstream. The methods of the present invention can be effected using composite compounds administered to a mammalian subject either alone or in combination as a pharmaceutical formulation.

Furthermore, the composite compounds of the present invention can be combined with pharmaceutically acceptable excipients and carrier materials such as inert solid diluents, aqueous solutions, or non-toxic organic solvents. If desired, these pharmaceutical formulations can also contain preservatives and stabilizing agents and the like, as well as minor amounts of auxiliary substances such as wetting or emulsifying agents, as well as pH buffering agents and the like which enhance the effectiveness of the active ingredient. The pharmaceutically acceptable carrier can be chosen from those generally known in the art including, but not limited to, human serum albumin, ion exchangers, dextrose, alumina, lecithin, buffer substances such as phosphate, glycine, sorbic acid, propylene glycol, polyethylene glycol, and salts or electrolytes such as protamine sulfate, sodium chloride, or potassium chloride. Those skilled in the art will appreciate that other carriers also may be used. Liquid compositions can also contain liquid phases either in addition to or to the exclusion of water. Examples of such additional liquid phases are glycerin, vegetable oils such as cottonseed oil, organic esters such as ethyl oleate, and water-oil emulsions.

The anti-emetic compositions of the present invention can be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art. Formulations suitable for parenteral administration, such as, for example, by intravenous, intramuscular, intradermal, and subcutaneous routes, include aqueous and non-aqueous isotonic sterile injection solutions. These can contain antioxidants, buffers, preservatives, bacteriostatic agents, and solutes that render the formulation isotonic with the blood of the particular recipient. Alternatively, these formulations can be aqueous or non-aqueous sterile suspensions that can include suspending agents, thickening agents, solublizers, stabilizers, and preservatives. Formulations of composite compounds suitable for use in methods according to the present invention can be presented in unit-dose or multi-dose sealed containers, or in physical forms such as ampules or vials.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

An "anti-emetic effective amount" of any embodiment of the present invention is determined using methods known to pharmacologists and clinicians having ordinary skill in the art. For example, an anti-emetic effective amount can be determined subjectively by administering increasing amounts of the pharmaceutical compositions of the present invention until such time the patient being treated reports diminished emesis, its associated nausea or gag reflex. Blood levels of the drug can be determined using routine biological and chemical assays and these blood levels can be matched to the route of administration. The blood level and route of administration giving the most desirable level of emesis relief can then be used to establish an "effective amount" of the pharmaceutical composition for treating the pain under study.

EXAMPLES

Bulk Composition

| Compound | Amount Per 100 260 mg Capsules |
| --- | --- |
| Lorazepam USP | 25 mg |
| Promethazine USP | 1250 mg |
| Diphenhydramine | 1250 mg |
| Metoclopramide USP | 1000 mg |
| Lactose monhydrate USP | 1000 mg |

Per Capsule Composition

| Compound | Amount Per 260 mg Capsules |
| --- | --- |
| Lorazepam USP | 0.25 mg |
| Promethazine USP | 12.50 mg |
| Diphenhydramine | 12.50 mg |
| Metoclopramide USP | 10.00 mg |
| Lactose monhydrate USP | 10.00 mg |

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A pharmaceutical composition comprising:

lorazepam, diphenhydramine, promethazine, and metoclopramide.

2. The pharmaceutical composition according to claim 1 further comprising a pharmaceutically acceptable carrier.

3. The pharmaceutical composition according to claim 2 wherein said pharmaceutically acceptable carrier is selected from the group consisting of corn starch, gelatin, lactose, acacia, sucrose, microcrystalline cellulose, kaolin, mannitol, dicalcium phosphate, calcium carbonate, sodium chloride, or alginic acid.

4. The pharmaceutical composition according to claim 2 further comprising disintegrators selected from the group consisting of microcrystalline cellulose, corn starch, sodium starch glycolate, and alginic acid.

5. The pharmaceutical composition according to claim 2 further comprising tablet binders selected from the group consisting of acacia, methylcellulose, sodium carboxymethylcellulose, polyvinylpyrrolidone, hydroxypropyl methylcellulose, sucrose, starch, and ethylcellulose.

6. The pharmaceutical composition according to claim 2 further comprising lubricants selected from the group consisting of magnesium stearates, stearic acid, silicone fluid, talc, waxes, oils, and colloidal silica.

7. The pharmaceutical composition according to claim 1 wherein said pharmaceutical composition is compounded in a form selected from the group consisting of tablets, capsules, powders, liquids, tonics, suppositories, transdermal devices, injectables, and inhalants.

8. A method of treating or inhibiting emesis in a patient comprising administering to said patient an anti-emetic effective amount of a pharmaceutical composition according to any one of claims 1 to 7.

9. A pharmaceutical composition comprising:

an broad-spectrum anti-emetic composition at least one antihistamine, at least anti-dopaminergic, and at least one anti-anxiety agent.

10. A pharmaceutical composition comprising:

a broad-spectrum anti-emetic composition comprising at least one benzodiapepine, at least one phenothiazine, at least one diphenhydramine, and at least one metoclopramide.

11. A pharmaceutical composition comprising:

the pharmaceutical compositions according to claim 9 or 10 further comprising a pharmaceutically acceptable carrier.

12. The pharmaceutical compositions according to claim 11 wherein said pharmaceutically acceptable carrier is selected from the group consisting of corn starch, gelatin, lactose, acacia, sucrose, microcrystalline cellulose, kaolin, mannitol, dicalcium phosphate, calcium carbonate, sodium chloride, or alginic acid.

* * * * *